United States Patent [19]

Takashima et al.

[11] Patent Number: 4,794,107

[45] Date of Patent: Dec. 27, 1988

[54] OINTMENT

[75] Inventors: Yasuji Takashima; Shigeo Tanaka, both of Ageo; Ichirou Kawamata, Kitamoto; Hiroshi Murayama, Houya, all of Japan

[73] Assignee: Taisho Pharmaceutical Co., Ltd., Tokyo, Japan

[21] Appl. No.: 906,653

[22] Filed: Sep. 12, 1986

Related U.S. Application Data

[63] Continuation of Ser. No. 574,021, Jan. 26, 1984, abandoned.

[30] Foreign Application Priority Data

Jan. 27, 1983 [JP] Japan .................... 57-11638

[51] Int. Cl.$^4$ .................... A61K 31/56; A61K 9/10; C07J 7/00; C07J 5/00
[52] U.S. Cl. .................... 514/179; 514/26; 514/943; 514/969
[58] Field of Search .................... 514/243, 179.26, 969

[56] References Cited

U.S. PATENT DOCUMENTS

| 4,289,764 | 9/1981 | Yarrow et al. | 514/179 |
| 4,290,962 | 9/1981 | Tachi et al. | 260/397.45 |
| 4,305,936 | 12/1981 | Klein | 514/179 |
| 4,407,824 | 10/1983 | Eckert | 514/886 |
| 4,551,475 | 11/1985 | Eckert | 514/408 |

FOREIGN PATENT DOCUMENTS

| 0069423 | 1/1983 | European Pat. Off. | 514/179 |
| 2514873 | 10/1976 | Fed. Rep. of Germany | 514/943 |

OTHER PUBLICATIONS

Chem. Abstracts Citation of Amundsen et al., vol. 95, 1981, 175671h.
McCutcheon's Detergents and Emulsifiers, 1982, pp. 120-121.

Primary Examiner—Ronald W. Griffin
Assistant Examiner—Nancy S. Carson
Attorney, Agent, or Firm—Wenderoth, Lind & Ponack

[57] ABSTRACT

An oily ointment comprising
(a) 0.01 to 0.5% by weight of hydrocortisone butyrate propionate,
(b) 2 to 10% by weight of a mixture of propylene glycol and purified water in a weight ratio of from 1:5 to 20:1,
(c) 0.1 to 6% by weight of a surface-active agent, and
(d) 75 to 97% by weight of a higher paraffinic hydrocarbon.

7 Claims, No Drawings

OINTMENT

This application is a continuation of now abandoned application Ser. No. 574,021, filed Jan. 26, 1984.

This invention relates to an ointment, and more specifically, to an oily ointment containing as a main ingredient (a main active ingredient) hydrocortisone butyrate propionate having excellent anti-inflammatory activity.

Hydrocortisone butyrate propionate is also known as 17α-butyryloxy-21-propionyloxy-11β-hydroxy-4-pregnene-3,20-dione, and is a known corticosteroidal compound having excellent anti-inflammatory activity which is topically administrable with little side-effects (see, for example, U.S. Pat. No. 4,290,962). An ointment prepared by blending hydrocortisone butyrate propionate with a higher paraffinic hydrocarbon such as white Vaseline has very low absorbability through the skin and is far from being satisfactory in practical applications. One conceivable means of increasing the absorbability of the main active ingredient through the skin is to blend it with the ointment base together with a good solvent for the active ingredient. For example, when hydrocortisone butyrate propionate is dissolved in a solvent such as propylene glycol, the resulting ointment has considerably increased skin absorbability, but the absorbability is still not entirely satisfactory.

The present inventors made extensive investigations in order to develop an ointment containing hydrocortisone butyrate propionate as an active ingredient and having higher skin absorbability. These investigations have led to the discovery that the use of a combination of propylene glycol, a good solvent for hydrocortisone butyrate propionate, and water, a non-solvent therefor, in a specified ratio can greatly improve the skin absorbability of an ointment containing the above active compound.

Thus, according to this invention, there is provided an oily ointment comprising (a) 0.01 to 0.5% by weight of hydrocortisone butyrate propionate,
(b) 2 to 10% by weight of a mixture of propylene glycol and purified water in a weight ratio of from 1:5 to 20:1,
(c) 0.1 to 6% by weight of a surface-active agent, and
(d) 75 to 97% by weight of a higher paraffinic hydrocarbon.

It should be understood that in the present specification and the appended claims, all percentages showing the concentrations of the ingredients of the ointment are based on the weight of the ointment.

One great characteristic of the ointment of this invention is to use a mixture of propylene glycol, a good solvent for hydrocortisone butyrate propionate, and purified water in a specified proportion. The "purified water", as used herein, denotes water obtained by distilling ordinary water (tap water or well water) or purifying it through an ion-exchange resin.

The weight ratio of propylene glycol to purified water in the mixture (b) should be within the range of from 1:5 to 20:1. If the weight ratio is lower than 1:5 or higher than 20:1, it is generally difficult to secure fully the effect of hydrocortisone butyrate propionate, the main active ingredient. The weight ratio of propylene glycol to purified water is preferably from 1:1 to 10:1, more preferably from 2:1 to 4:1.

The mixture (b) having the aforesaid composition can be present in the ointment of this invention in a concentration of 2 to 10% by weight, preferably 3 to 6% by weight, more preferably 4 to 5% by weight.

The surface-active agent as one ingredient of the ointment of this invention may be any of those surface-active agents which have been previously used in preparing oily ointments. In particular, non-ionic surface-active agents such as sorbitan fatty acid esters (e.g. polyoxyethylene sorbitan fatty acid esters), glycerin fatty acid esters and propylene glycol fatty acid esters are suitable. More specifically, those commercially available under the tradenames Nikkol TS10, S010, MGS and PMS made by Nikko Chemicals Co., Ltd., Japan can be advantageously used. These surface-active agents may be used singly or in combination. Generally, it is desirable to use one or more surfactants having a total HLB within the range of 2.0 to 13.0, preferably 3.0 to 7.0. Sorbitan monooleate and propylene glycol monostearate are especially preferred in the present invention.

The surface-active agent is present in the ointment of this invention in a concentration of 0.1 to 6% by weight, preferably 0.5 to 2.5% by weight, depending upon the kind of surface-active agent.

The higher paraffinic hydrocarbon used as a base of the oily ointment of this invention includes any pharmaceutically acceptable paraffinic hydrocarbons which are ordinarily used in the preparation of oily ointments, and is generally one, or a mixture, of straight or branched saturated aliphatic hydrocarbons having 16 to 40 carbon atoms. Specific examples of such higher paraffinic hydrocarbons are light liquid paraffin, liquid paraffin, white Vaseline (petrolatum), yellow Vaseline, paraffin and ceresin. The base must have a viscosity suitable for skin coatability of the ointment. Desirably, the base has a viscosity of generally about $10^2$ to about $10^6$, preferably about $10^3$ to $10^5$, centipoises at 20° C. Accordingly, when the above-exemplified higher paraffinic hydrocarbons, if used singly, do not provide a viscosity in the above range, it is desirable to adjust the viscosity by combining two or more of such higher paraffinic hydrocarbons. An especially preferred combination is a mixture of liquid paraffin and white Vaseline in a weight ratio of from 1:1 to 1:3.

The higher paraffinic hydrocarbon described above forms a base of the ointment of this invention and is used in a concentration of 75 to 97% by weight, preferably 80 to 95% by weight.

In addition to the above essential ingredients the ointment of this invention may further include other pharmacologically effective substances in specified concentrations, for example 0.1 to 0.5% by weight of gentamicin sulfate, 0.1 to 0.5% by weight of fradiomycin sulfate, 0.1 to 1% by weight of tetracycline, 5 to 10% by weight of crotamiton (crotonyl-N-ethyl-o-toluidine), etc. As required, the ointment of this invention may further contain 1 to 5% by weight of a moisture-retaining agent (such as urea, sodium lactate, pyrrolidonecarboxylic acid, and glycerol), a small amount of a pH adjusting agent (such as citric acid and phosphoric acid), a small amount of a perfume, etc.

The concentration of hydrocortisone butyrate propionate, as the main active ingredient of the ointment of this invention, is 0.01 to 0.5% by weight, preferably 0.025 to 0.2% by weight.

The ointment of this invention can be prepared by methods known per se. For example, it can be formulated by dissolving hydrocortisone butyrate propionate in propylene glycol at an elevated temperature of about 50° to about 80° C., adding the solution to a mixture of the heat-melted higher paraffinic hydrocarbon and the surface-active agent, if required together with the aforesaid optional ingredients, mixing them with stirring at an elevated temperature of about 40° to about 80° C., adding purified water, stirring the mixture at an elevated temperature until the mixture becomes fully uniform, and then cooling the mixture with stirring. Alternatively, purified water may be added to the propylene glycol solution of hydrocortisone butyrate propionate. Desirably, however, purified water is added in the final stage as in the aforesaid method of preparation.

The ointment of this invention permits very good skin absorbability of hydrocortisone butyrate propionate as the active ingredient, and is very effective for the curing and treatment of diseases involving inflammation, such as acute eczema, chronic eczema, seborrheic eczema, atopic dermatitis, infantile eczema, contact dermatitis and psoriasis vulgaris.

In the curing and treatment of these inflammatory diseases, the ointment of this invention may be topically applied to the lesion. The amount of the ointment to be applied differs depending upon the concentration of the active ingredient of the ointment. Generally, a suitable amount of the ointment is applied to the lesion once to several times a day depending upon the severity of the disease treated.

The excellent skin absorbability of the ointment of this invention can be illustrated by the following test example.

TEST EXAMPLE

Ointments of the recipes shown in Table 1 (samples A, B, C, D and E) were prepared in accordance with the procedure shown in Example 1 given hereinafter.

TABLE 1

| | Ointment recipes (g) | | | | |
| --- | --- | --- | --- | --- | --- |
| | Sample | | | | |
| Ingredient | A | B | C | D | E |
| Hydrocortisone butyrate propionate | 0.1 | 0.1 | 0.1 | 0.1 | 0.01 |
| Propylene glycol | — | 5.0 | 4.0 | 2.5 | 4.0 |
| Purified water | — | — | 1.0 | 2.5 | 1.0 |
| Nikkol TS 10 (polyoxyethylene sorbitan monostearate) | — | 0.5 | 0.5 | 0.5 | 0.5 |
| Nikkol PMS (propylene glycol monostearate) | — | 2.0 | 2.0 | 2.0 | 2.0 |
| Liquid paraffin | 10.0 | 10.0 | 10.0 | 10.0 | 10.0 |
| White Vaseline | 89.9 | 82.4 | 82.4 | 82.4 | 82.49 |
| Total | 100.0 | 100.0 | 100.0 | 100.0 | 100.00 |

Twenty healthy male adults were selected as subjects. About 50 mg of each of the samples was coated on adhesive tapes for patch testing (made by Torii Pharmaceutical Co., Ltd.; small size), and the adhesive tapes were applied to the forearms of the individual subjects. Four hours later, the adhesive tapes were removed, and the samples remaining on the skin were well wiped off with a gauze impregnated with 70% ethanol.

The vasoconstricting reaction was examined 2 hours, 4 hours, and 20 hours after removal of the samples, and the degree of the reaction was evaluated in four grades and expressed by average points.

++: Became exceedingly pale and white ... 3 points
+: Became clearly pale and white ... 2 points
±: Became slightly pale and white ... 1 point
—: Did not become pale and white at all ... 0 point The results are tabulated in Table 2.

TABLE 2

| | Vasoconstricting action | | |
| --- | --- | --- | --- |
| | Time elapsed after removal of the sample | | |
| Sample | 2 hours | 4 hours | 20 hours |
| A | 0.85 | 1.05 | 0.1 |
| B | 2.0 | 2.15 | 0.5 |
| C | 2.35 | 2.40 | 0.7 |
| D | 2.25 | 2.35 | 0.55 |
| E | 2.05 | 2.15 | 0.55 |

It is clear from the results given in Table 2 that the ointments of the invention (samples C to E) have improved skin absorbability of the main active ingredient relative to the comparative ointments (samples A and B) prepared in accordance with a customary method. In particular, sample E shows equivalent skin absorbability to sample B in spite of the fact that the concentration of the main active ingredient of sample E is one-tenth of that of sample B. These results clearly show that the absorbability of the ointment of this invention through the skin is very high.

The following Examples illustrate the preparation of the ointment of this invention.

EXAMPLE 1

White Vaseline (94.4 g) and 0.5 g of Nikkol S010 (sorbitan monooleate) were melted at 70° C. to prepare an oil component A. Then, 0.1 g of hydrocortisone butyrate propionate was dissolved in 4.0 g of propylene glycol at 60° C., and the solution was added to the oil component A. Furthermore, 1.0 g of purified water was added, and the mixture was stirred to disperse the ingredients fully. The mixture was cooled with stirring to form 100 g of an ointment.

EXAMPLE 2

| Hydrocortisone butyrate propionate | 0.01 g |
| --- | --- |
| Propylene glycol | 1.0 g |
| Purified water | 3.0 g |
| Nikkol TS 10 (polyoxyethylene sorbitan monostearate) | 0.5 g |
| Nikkol PMS (propylene glycol monostearate) | 2.0 g |
| Liquid paraffin | 10.0 g |
| White Vaseline | balance |
| Total | 100 g |

An ointment was prepared in accordance with the above recipe by the same procedure as in Example 1.

EXAMPLE 3

| Hydrocortisone butyrate propionate | 0.5 g |
| --- | --- |
| Propylene glycol | 5.0 g |
| Purified water | 0.5 g |
| Nikkol TS 10 (polyoxyethylene sorbitan monostearate) | 0.1 g |
| Nikkol MGS (glycerin monostearate) | 2.0 g |
| Liquid paraffin | 10.0 g |
| White Vaseline | balance |
| Total | 100 g |

An ointment was prepared in accordance with the above recipe by the same procedure as in

EXAMPLE 1.

What we claim is:

1. A oily ointment consisting essentially of:
   (a) 0.01 to 0.5% by weight of hydrocortisone butyrate propionate,
   (b) 2 to 10% by weight of a mixture of propylene glycol and purified water in a weight ratio of from 1:1 to 10:1,
   (c) 0.1 to 6% by weight of a surface-active agent component having a total HLB of 3.0 to 7.0 consisting of a member selected from the group consisting of a sorbitan fatty acid ester, a glycerin fatty acid ester, a propylene glycol fatty acid ester, and a mixture thereof, said surface-active agent component being the only surface-active agent component in the ointment, and
   (d) 75 to 97% by weight of a higher paraffinic hydrocarbon component selected from the group consisting of light liquid paraffin, liquid paraffin, white petrolatum, yellow petrolatum, paraffin, ceresin and a mixture thereof.

2. The ointment of claim 1, which contains the mixture (b) in a concentration of 3 to 6% by weight.

3. The ointment of claim 1 wherein the concentration of the surface-active agent component is 0.5 to 2.5% by weight.

4. The ointment of claim 1 wherein the higher paraffinic hydrocarbon component has a viscosity of $10^2$ to $10^6$ centipoises at 20° C.

5. The ointment of claim 1 wherein the concentration of the higher paraffinic hydrocarbon component is 80 to 95% by weight.

6. The ointment of claim 1 wherein the higher paraffinic hydrocarbon component is a mixture of liquid paraffin and white petrolatum in a weight ratio of from 1:1 to 1:3.

7. The ointment of claim 1 wherein the sorbitan fatty acid ester is a polyoxethylene sorbitan fatty acid ester.

* * * * *

UNITED STATES PATENT AND TRADEMARK OFFICE
CERTIFICATE OF CORRECTION

PATENT NO. : 4,794,107
DATED : December 27, 1988
INVENTOR(S) : Yasuji TAKASHIMA et al.

It is certified that error appears in the above-identified patent and that said Letters Patent is hereby corrected as shown below:

In the heading of the patent, under item [30] entitled Foreign Application Priority Data, change the number for the Japanese priority application to:

--58-11638--.

Signed and Sealed this

Thirteenth Day of June, 1989

Attest:

DONALD J. QUIGG

*Attesting Officer*  *Commissioner of Patents and Trademarks*